(12) United States Patent
Warner et al.

(10) Patent No.: US 9,398,987 B2
(45) Date of Patent: Jul. 26, 2016

(54) METHOD OF PRINTING GRAPHICS ON ABSORBENT-ARTICLES

(75) Inventors: Alrick Vincent Warner, Loveland, OH (US); Timothy Wayne Roberston, Cincinnati, OH (US); Beth Goldman Mason, Cincinnati, OH (US); George Christopher Dobrin, Mason, OH (US); Rachel Eden Walther, Union, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 527 days.

(21) Appl. No.: 13/457,562

(22) Filed: Apr. 27, 2012

(65) Prior Publication Data

US 2013/0289511 A1    Oct. 31, 2013

Related U.S. Application Data

(63) Continuation of application No. 13/156,583, filed on Jun. 9, 2011, now abandoned, and a continuation of application No. 13/156,954, filed on Jun. 9, 2011, now Pat. No. 8,652,214, and a continuation of application No. 13/185,543, filed on Jul. 19, 2011, now abandoned.

(60) Provisional application No. 61/368,071, filed on Jul. 27, 2010, provisional application No. 61/368,252, filed on Jul. 27, 2010, provisional application No. 61/368,255, filed on Jul. 27, 2010.

(51) Int. Cl.
| | |
|---|---|
| *G06K 15/00* | (2006.01) |
| *A61F 13/84* | (2006.01) |
| *A61F 13/513* | (2006.01) |
| *A61F 13/514* | (2006.01) |
| *B41F 33/00* | (2006.01) |

(52) U.S. Cl.
CPC ........... *A61F 13/84* (2013.01); *A61F 13/51394* (2013.01); *A61F 13/51496* (2013.01)

(58) Field of Classification Search
CPC .............. A61F 13/84; A61F 13/51496; A61F 13/51394; H04N 1/0066; G06K 15/1885; G06K 3/125; G06F 17/212
USPC ............ 358/1.1, 1.12, 1.13, 1.14, 1.15, 1.18; 101/483; 604/385.01; 705/500
See application file for complete search history.

(56) References Cited

U.S. PATENT DOCUMENTS

| | | |
|---|---|---|
| 3,842,837 A | 10/1974 | Sward |
| 4,615,695 A | 10/1986 | Cooper et al. |

(Continued)

FOREIGN PATENT DOCUMENTS

| | | |
|---|---|---|
| EP | 0547497 A2 | 6/1993 |
| EP | 1552802 A1 | 7/2005 |

(Continued)

OTHER PUBLICATIONS

International Search Report, PCT/IB2007/054482, mailed Aug. 4, 2008, 14 pages.

(Continued)

*Primary Examiner* — Gabriel Garcia
(74) *Attorney, Agent, or Firm* — Andrew A Paul

(57) ABSTRACT

Absorbent articles having graphics disposed upon them and methods of printing graphics. The graphics are suitable for or actually embodied in fabric and may be visually coordinated to clothing. The clothing may be an article of clothing and/or a line of clothing.

22 Claims, 10 Drawing Sheets

(56) References Cited

U.S. PATENT DOCUMENTS

| | | |
|---|---|---|
| 4,649,573 A | 3/1987 | Yen |
| 5,591,151 A | 1/1997 | Hasse et al. |
| 5,924,131 A | 7/1999 | Wilkinson |
| 6,045,543 A | 4/2000 | Pozniak et al. |
| 6,219,452 B1 | 4/2001 | Nair et al. |
| 6,297,424 B1 | 10/2001 | Olson et al. |
| 6,307,119 B1 | 10/2001 | Cammarota et al. |
| 6,352,528 B1 | 3/2002 | Weber et al. |
| 6,564,118 B1 | 5/2003 | Swab |
| 6,635,797 B2 | 10/2003 | Olson et al. |
| 6,702,795 B2 | 3/2004 | Klemp |
| 6,859,679 B1 | 2/2005 | Smith et al. |
| 7,657,340 B2 | 2/2010 | Lind |
| 2003/0073966 A1 | 4/2003 | Sosalla et al. |
| 2005/0015066 A1* | 1/2005 | Anderson et al. ............. 604/358 |
| 2005/0096614 A1 | 5/2005 | Perez et al. |
| 2005/0101931 A1 | 5/2005 | Bryant et al. |
| 2005/0124954 A1 | 6/2005 | Adams et al. |
| 2005/0143698 A1 | 6/2005 | Sosalla et al. |
| 2005/0154365 A1 | 7/2005 | Zander et al. |
| 2006/0069372 A1 | 3/2006 | Chakravarty et al. |
| 2006/0167428 A1 | 7/2006 | Denti et al. |
| 2006/0173428 A1 | 8/2006 | Acors |
| 2006/0246263 A1 | 11/2006 | Yahiaoui et al. |
| 2006/0247594 A1 | 11/2006 | Nickel et al. |
| 2008/0058748 A1 | 3/2008 | Seifert et al. |
| 2008/0082071 A1 | 4/2008 | Bryant et al. |
| 2008/0108967 A1 | 5/2008 | Mizushima et al. |
| 2008/0234643 A1 | 9/2008 | Kaneda |
| 2009/0040569 A1* | 2/2009 | Hamzy ......................... 358/488 |
| 2009/0247979 A1 | 10/2009 | Sosalla et al. |
| 2009/0260123 A1 | 10/2009 | Swift |
| 2009/0287173 A1* | 11/2009 | Sosalla et al. ................. 604/361 |
| 2012/0016327 A1 | 1/2012 | Mason et al. |
| 2012/0016762 A1 | 1/2012 | Glahn et al. |
| 2012/0024177 A1 | 2/2012 | Warner et al. |
| 2012/0029457 A1 | 2/2012 | Mason et al. |
| 2012/0030145 A1 | 2/2012 | Mason et al. |

FOREIGN PATENT DOCUMENTS

| | | |
|---|---|---|
| EP | 1704842 A1 | 9/2006 |
| JP | 2003-070838 A | 3/2003 |
| WO | WO 03/032884 A1 | 4/2003 |
| WO | WO 2005/014297 A1 | 2/2005 |
| WO | WO 2005/065620 A1 | 7/2005 |
| WO | WO 2006/083595 A2 | 8/2006 |
| WO | WO 2007/018724 A1 | 2/2007 |
| WO | WO 2007/024327 A1 | 3/2007 |
| WO | WO 2008/056315 A1 | 5/2008 |

OTHER PUBLICATIONS

International Search Report, PCT/US2011/045321, mailed Oct. 7, 2011, 11 pages.

International Search Report, PCT/US2011/045315, mailed Oct. 13, 2011, 12 pages.

International Search Report, PCT/US11/045134, mailed Dec. 14, 2011, 10 pages.

"Pampers & Cynthia Rowley Partner on the First 'Designed' Diaper", Jun. 30, 2010, 2 pages.

* cited by examiner

METHOD OF PRINTING GRAPHICS ON ABSORBENT-ARTICLES

CROSS REFERENCE TO RELATED APPLICATIONS

This application: is a continuation of and claims the benefit of U.S. application Ser. No. 13/156,583, filed on Jun. 9, 2011, which in turn claims the benefit of U.S. Provisional Application No. 61/368,071, filed on Jul. 27, 2010; and is a continuation of and claims the benefit of U.S. application Ser. No. 13/156,954, filed on Jun. 9, 2011, which in turn claims the benefit of U.S. Provisional Application No. 61/368,252, filed on Jul. 27, 2010; and is a continuation of U.S. application Ser. No. 13/185,543, filed on Jun. 9, 2011, which in turn claims the benefit of U.S. Provisional Application No. 61/368,255, filed on Jul. 27, 2010; the substances of each of which are hereby incorporated by reference.

FIELD OF THE INVENTION

In one aspect, the invention relates generally to absorbent articles having graphics disposed upon them and methods of printing graphics. The graphics are suitable for or actually embodied in fabric and may be visually coordinated to clothing. The clothing may be an article of clothing and/or a line of clothing.

BACKGROUND OF THE INVENTION

Absorbent articles are used commonly. In many cases, e.g. diapers, the purchaser of the absorbent article is not the end user of the article. Many factors influence the purchaser's decision to purchase particular absorbent articles, non-limiting examples of which include: price and product performance, e.g. absorbency, ease of fastening/refastening, tactile feel against the skin, etc. The aesthetics of an absorbent article have become an increasingly important factor in driving purchase decision-making. Many purchasers prefer to have colors, patterns, and/or other designs employed by the absorbent article. This creates a need to provide desirable graphics without having an unacceptably negative impact on other decision factors, such as price and absorbency.

Although absorbent articles bearing graphics are known, these graphics are not designed to be visually coordinated to a particular article of clothing or to a particular line of clothing. Purchasers increasingly prefer absorbent articles with graphics, and it is believed that some purchasers would prefer absorbent articles with graphics that have a similar appearance to particular articles of clothing and/or lines of clothing. It is known for an absorbent article to bear a graphic that generically looks like a "type of clothing", e.g. blue jeans; however, it is not known to coordinate the graphics on an absorbent article to the graphics on actual articles of clothing, e.g. a particularly patterned and/or colored outfit that is sold as a clothing item, or a series of related clothing items that constitute a line of clothing, e.g. the Jane Doe collection, sold by a particular retailer. Accordingly, there is a need for such absorbent articles.

SUMMARY OF THE INVENTION

In one aspect, the invention relates generally to absorbent articles having graphics disposed upon them and methods of printing graphics. The graphics are suitable for or actually embodied in fabric and may be visually coordinated to clothing. The clothing may be an article of clothing and/or a line of clothing.

It is an object of this invention to provide absorbent articles bearing at least one graphic, and methods of printing and selling the absorbent articles, wherein at least one visual characteristic of the at least one graphic is visually coordinated to at least one visual characteristic of an article of clothing and/or a line of clothing. It is an object of this invention to provide absorbent articles bearing at least one graphic, wherein at least one visual characteristic of the at least one graphic is visually coordinated to at least one visual characteristic of a line of clothing. It is an object of this invention to provide absorbent articles bearing at least one graphic, wherein at least one visual characteristic of the at least one graphic is visually coordinated to at least one visual characteristic of a particular article of clothing, i.e. not a type of clothing or a genre of clothing. It is an object of this invention to provide a method of printing graphics on absorbent articles where the graphics comprise designs inspired by designs suitable for or actually embodied in fabric. It is an object of this invention to provide a method of printing with increased detail resolution. It is an object of this invention to provide a method of printing with improved color-to-color register. It is an object of this invention to provide a method of printing with thinner line weight. These and other objects, features, and advantages of the invention will become more apparent upon reading the following specification in conjunction with the accompanying drawing figures.

DETAILED DESCRIPTION OF THE INVENTION

Figure 1A:
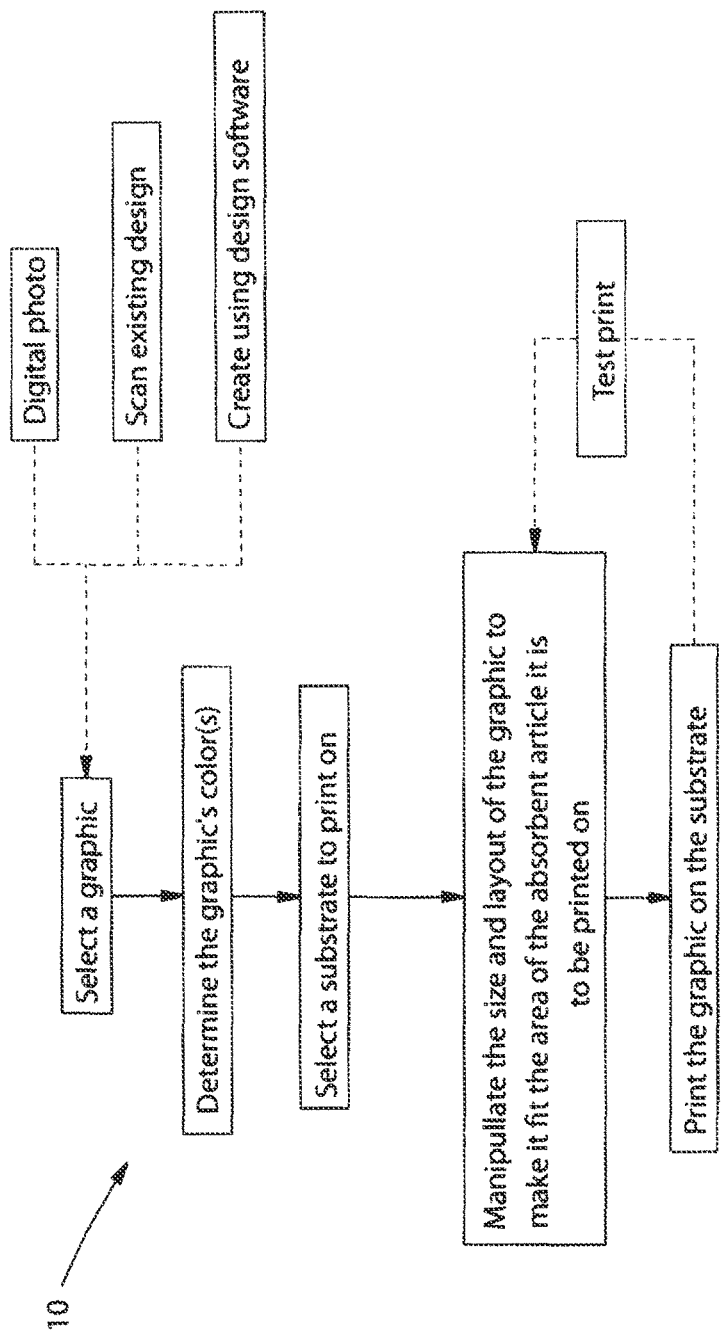
FIG. 1A is a flowchart of a method of printing graphics on absorbent articles suitable for use with the present invention.

In one aspect, the invention is intended primarily for use with absorbent articles. As used herein, the term "absorbent article" refers to devices which absorb and contain body exudates, and, more specifically, refers to devices which are placed against or in proximity to the body of the wearer to absorb and contain the various exudates discharged from the body. As used herein, the term "diaper" refers to an absorbent article generally worn by infants and incontinent persons that is worn about the lower torso of the wearer. It should be understood, however, that the invention is also applicable to other absorbent articles such as incontinence briefs, incontinence undergarments, incontinence pads, diaper holders and liners, feminine hygiene garments, feminine hygiene pads, feminine hygiene pantiliners, tampons, and the like. As used herein, the term "disposable" refers to absorbent articles that generally are not intended to be laundered or otherwise restored or reused as absorbent articles, i.e. they are intended to be discarded after a single use, and preferably, to be recycled, composted, or otherwise disposed of in an environmentally compatible manner. In an embodiment, the absorbent articles for which the invention is primarily intended for use, are disposable absorbent articles.

In an embodiment of the invention, the method described herein is used to print one or more graphics for an absorbent article. In another embodiment, the graphics match one or more graphics on a particular article of clothing. In yet another embodiment, the graphics match one or more graphics on articles of clothing that comprise a line of clothing.

Absorbent articles may typically comprise a topsheet having a bodyfacing surface and a garment facing surface, a backsheet having a bodyfacing surface and a garment facing surface, and an absorbent core disposed between the garment facing surface of the topsheet and the bodyfacing surface of the backsheet. In an embodiment, the graphics created by the method disclosed herein are disposed upon the bodyfacing surface of the topsheet. In another embodiment, the graphics are disposed upon the garment facing surface of the topsheet. In another embodiment, the graphics are disposed upon the garment facing surface of the backsheet. In yet another embodiment, the graphics are disposed upon both the bodyfacing surface of the topsheet and the garment facing surface of the backsheet. Other absorbent articles, e.g. catamenial tampons, may typically comprise a compressed absorbent core disposed within an overwrap substantially covering the exterior surface of the compressed absorbent core, the overwrap having a core facing surface and a bodyfacing surface. In an embodiment, the graphics created by the method disclosed herein are disposed upon the core facing surface of the overwrap. In another embodiment, the graphics are disposed upon the bodyfacing surface of the overwrap. In yet another embodiment, the graphics are disposed upon both the core facing surface of the overwrap and the bodyfacing surface of the overwrap. In an embodiment, the overwrap comprises a non-woven material.

In an embodiment, the invention provides a method of selling absorbent articles bearing at least one graphic, wherein at least one visual characteristic of the at least one graphic is visually coordinated to at least one visual characteristic of an article of clothing and/or a line of clothing. The graphic and the clothing each has at least a first, and preferably additional visual characteristics, wherein the visual characteristics of the graphic are matched the corresponding visual characteristics of the clothing. In other embodiments, there are at least 2, preferably at least 3, visual characteristics that are matched. In yet other embodiments, there are at least 4, preferably at least 5, visual characteristics that are matched. In still other embodiments, there are at least 6, preferably at least 7, visual characteristics that are matched. In yet other embodiments, there are at least 8, preferably at least 9, visual characteristics that are matched.

In an embodiment, an absorbent article appears visually coordinated to an article of clothing, and/or a line of clothing, to a consumer. An absorbent article will be visually coordinated when one or more its visual characteristics are matched with the corresponding visual characteristics of the article of clothing, and/or line of clothing. These visual characteristics may be visible patterns of color. The color of these patterns can be described by the value of the hue, saturation, and luminosity. This color will be determined from the visible spectral and angular distribution of light coming from an object. The patterns can be described by their location, extent, shape, and orientation. These patterns may have smaller patterns contained within them. The pattern may be the result of the non-uniform chemical composition of the element like the printing of a pattern of a dye or from the texture of the element like the embossing of a pattern. The pattern will be determined from the visible spatial, spectral and angular distribution of light coming from an object.

As used herein, the term "visual characteristic" is intended to mean a visible, distinguishing or recognizable feature or attribute of a visible aspect of one or more elements of an absorbent article and/or an article of clothing, and/or a line of clothing. Non-limiting examples of visual characteristics are color, texture, pattern, form, and the like.

As used herein, the term "visible" is intended to mean attribute of feature which is visually perceived by an individual user or consumer. Generally for a consumer or user, the attribute should be visible in the range of about 0.25 feet (0.075 meters) to about 3 feet (0.91 meters). For a non-consumer or non-user, generally for an attribute to be visible, the distance will typically be greater than about 3 feet (0.91 meters). As used herein, "perceived" or "perception" is the ability to recognize an attribute or feature when the visual angle that the attribute or feature subtends is greater than about 5 minutes of visual arc and less than about 45 minutes of visual arc as determined by the following equation: Minutes of visual arc=3438*(length of the object/distance from object); wherein the length of the object=size of the object measured perpendicular to the line of sight, the distance from object=distance from the front of the eye to the object along the line of sight, and a minute of visual arc is $\frac{1}{60}^{th}$ of 1 degree.

As used herein, the term "color" is intended to mean an individual's perception of the spectral composition of visible light coming from a portion of an object. Color characteristics include hue, saturation and luminosity. Each is a separate color characteristic. Hue is the attribute of a color which allows it to be classified as a given color. Saturation, which is sometimes referred to as vividness, is the intensity of the color. Saturation is the degree of freedom from gray. Luminosity, sometimes referred to as value, is the degree of lightness (paleness) or darkness in a color. For example, a blue with white added is a pale color, e.g. baby blue and blue with black added is a dark color, e.g. navy blue. A measurement of hue, saturation and luminosity are described in more detail below.

As used herein, the term "form" is used to describe an individual's perception of the spatial variation of visible light due to the bulk shape and structure of a portion of an object in three dimensions. Stated another way, form is shape and structure of an item which distinguishes it from its surrounding which causes a spatially discontinuous change in light that is transmitted through or reflected from an item.

As used herein, the term "texture" is used to describe the individual's perception of the spatial variation of visible light due to surface structure of a portion of an object in two dimensions. Textures can be visual effects generated by surface roughness and visual illusion created by mere color or pattern. Texture may be the result of the natural characteristics of a given material as a result of the material formation process. Textures may also be imparted to a material using techniques known to those skilled in the art including, for example, printing, embossing, bonding, aperturing and the like.

As used herein, the term "pattern" is used to describe the individual's perception of spatial variation of visible light due to contrasts in spatial variation of light due to the color, form, and texture of a portion of an object incorporated into the object by the manufactory of the elements. This contrast creates various visual distinct regions or lines sometimes referred to as "figures" within its surrounding sometimes referred to as "ground." Patterns can be formed by combinations of contrasting color, form, and texture relative to its surroundings. An element can have more than one pattern, but each pattern would be distinguishable, recognizable, and separate from the other patterns on the element. Pattern is also a term used to describe the observer's perception of combined effect of more than one color, form, or texture within a portion of an observer's field of view. Patterns may have a "length", "extent", "shape", "position" and "orientation". Each is a pattern characteristic within the scope of the present invention. Length is the perceived distance along the major axis of the pattern. The "major axis" is the axis of the longest symmetry. The extent of the pattern is the area of the pattern. Shape is simply the shape of the pattern. Position is the location of the pattern relative to its surroundings. And orientation is position of the major axis of the pattern relative to its surroundings.

As used herein, the term "match" or "matched" is used to describe the way or degree two items visually fit together. For example, two items are considered matched if some aspects of one of the items are identical to similar aspects of another item. In one form of match, two items resemble each other are said to match.

As used herein, the term "coordinate" or "coordination" is used to describe how two components or elements of the absorbent article and the article of clothing, and/or line of clothing visually belong together. Visual characteristics are said to coordinate if one aspect of the visual characteristic is the same or falls within limits described with this specification. Visual characteristics are also said to coordinate if they match. Components or elements are considered to be coordinated if they match. Graphics are considered to be coordinated if they match. An absorbent article and an article of clothing are considered to be coordinated if they match. An absorbent article and a line of clothing are considered to be coordinated if they match. Colors may be coordinated if they have a hue, luminosity or saturation that match within limits described below.

As used herein, the term "nonwoven fabric or web" means a web having a structure of individual fibers or threads which are interlaid, but not in a regular or identifiable manner as in a knitted or woven fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, airlaying processes and bonded carded web processes. The basis weight of nonwoven fabrics is usually expressed in ounces of material per square yard (osy) or grams per square meter (gsm) and the fiber diameters useful are usually expressed in microns.

Coordination may be achieved using certain combinations of visual characteristics which unite or harmonize the appearance of an absorbent article with an article of clothing and/or a line of clothing. Coordination may be achieved by matching visual characteristics of the absorbent article and clothing components. As described above, visual characteristics are features or characteristics that are discernible by sight during the normal use of the product. Examples of different types of visual characteristics, which may be employed in the present invention include, without limitation, color, form, texture, pattern, transmittance/opacity, gloss, and sheen, among others.

Of the visual characteristics, color is a characteristic that is simple to quantify. Colors have some basic characteristics, including hue, saturation, and luminosity. Each of these terms is described above. A given color may be varied by changing the saturation and luminosity. Saturation is changed by adding a neutral color, black, white, or gray. Luminosity may be changed by adding a brightener to a given color. In the present invention, if two colors have the same hue, whether or not they are different in saturation or luminosity, the two colors are considered coordinated. Likewise, if two colors have the same saturation or the same luminosity, the colors are considered to be coordinated. Colors which have the same hue, saturation and luminosity are considered matched. Color may be imparted by any means know to those skilled in the art, including, for example, printing, dyeing, pigmenting and the like.

Form may be accomplished by techniques know to those skilled in the art. Form can be construed on the simplest scale as shape. Shape may be imparted to the components by known methods such as cutting and the like. By using the term "shape" in this context, it is intended that the outline, edges and the like have a shape in addition to a linear outline. Generally, shapes are considered the same if the aspects of one shape are proportional to another shape. For example, in the case of a triangle, if all the angles are identical in two different triangles, but the sides are different in length, the two triangles are considered to be coordinated since they have the same proportions relative to each other. Stated another way, shapes are considered to be coordinated if the shapes are the same or are proportional to each other.

Textures can be visual effects generated by rough surfaces, and or differences in the surface characteristics, or visual illusions created by mere color or pattern. Texture may be the result of the natural characteristics of a given material as a result of the material formation process. Textures may also be imparted to a material using known techniques known to those skilled in the art including, for example, printing, embossing, bonding, aperturing and the like.

One or more objects, one or more geometric and non-geometric shapes and/or one or more colors having some relationship with one another may achieve patterns. Patterns may be random or repeating. Repeating patterns will typically have objects, shapes, and/or colors in a given frequency or spacing. Patterns can be achieved by repeating a single object, or shape or can be achieved by repeating multiple objects or shapes. Repeating or alternating two or more colors with a given frequency may also create patterns. Patterns may be formed by using techniques including, for example, printing, embossing, bonding, aperturing and the like.

Any known printing method may be used so long as a pattern or a texture can be imparted to the surface being printed. Such methods for printing are described briefly in FIGS. 1A and 1B.

Embossing may be accomplished, for example, by passing a material between a heated or non-heated anvil roll and a heated or non-heated embossing roll, with the embossing roll containing a pattern. Other techniques for imparting patterns or texture include, for example, aperturing, creating layers, orientation of materials, bonding patterns and the like. Texture can also be created by selection of materials having the same or similar visual characteristic, beyond color, and patterns imposed on the material.

In an embodiment, the invention provides a method of selling absorbent articles bearing at least one graphic, wherein at least one visual characteristic of the at least one graphic is visually coordinated to at least one visual characteristic of an article of clothing and/or a line of clothing. As an example, a child's dress has a pattern of purple printed flowers thereon and an element of the absorbent article, for example the backsheet of a diaper, may have the same pattern of purple flowers printed thereon. The pattern of flowers is a first visual characteristic and the purple hue of the flowers is a second visual characteristic. As a result, the absorbent article is coordinated with the article of clothing due to the presence of the pattern of purple flowers on both components. Coordination of the product in the present invention is obtained by having one or more visual characteristics that match. While the present specification describes the invention in terms of at least one visual characteristic, this does not mean that there cannot be two or more visual characteristics creating the desired coordination affect. In fact, the more shared visual characteristic there are, the more the items appear to be coordinated. In the present invention, there may be two, three, four, five, six, seven, eight, nine or more visual characteristic which are coordinated. In one embodiment, there are at least 2, preferably at least 3, more preferably at least 4, visual characteristics that are coordinated.

In an embodiment, a first and second visual characteristic are different in some aspect from each other. It is possible for the visual characteristics to be two different colors, a color and a pattern, a texture and a color, a texture and a pattern, two different patterns, two different textures and the like. If there are three characteristics which are different, then there could be two different colors and a pattern; three different colors; a color, a pattern and a texture; among many other combinations.

In an embodiment, white is generally not considered as a color is used as the coordinating feature if white is a predominate color on the element being coordinated. This is because white is the predominate color of absorbent articles, and thus white does not lend itself as a coordinating color. However, white may be a coordinating color, provided that it is not used as the predominate color on the components or surfaces being coordinated. Stated another way, white may be a coordinating color if it is used as an accent or a non-dominate color. By "non-dominate color" it is intended mean a color which encompasses less than 50%, desirable less that 30%, of the surface area of a surface.

In an embodiment, the first and second visual characteristics may be configured as first and second colors. Each of the first and second colors may be different from one another by having a different hue. One or more colors may also be different by virtue of having a different luminosity and/or saturation/vividness. Saturation/vividness is the intensity of the color from pale to dark. Colors of different hues can be coordinated or match by virtue of having the same luminosity or saturation. For example, pale or pastel colors of different hues tend to blend together or appear that they belong together or are matched due to the fact that the saturation levels are similar. Other factors in color differences include different finishes e.g. gloss/finish verses a matte finish. Matte finishes tend to diffuse or scatter light compared to a gloss finish, which is specular.

Printing may generally be characterized as an industrial process in which an image is reproduced on a substrate, such as paper, polyolefin film, or nonwoven fabric. There are various classes of printing processes, which may include stencil and screen printing, relief printing, planographic printing, intaglio printing, and electronic printing. Stencil and screen printing may be used for printing T-shirts, signage, banners, billboards, and the like. Examples of relief printing may include letterpress and flexography. Examples of planographic printing may include offset lithography, screenless lithography, collotype, and waterless printing. In addition, examples of intaglio printing may include gravure, steel-die, and copper-plate engraving. Examples of electronic printing may include electrostatic, magnetographic, ion or electron deposition, and ink-jet printing. It is it to be appreciated that various types of printing processes may be used to create the graphics disclosed herein. For example, in some embodiments, it may be preferable to use flexography. In particular, flexography may utilize printing plates made of rubber or plastic with a slightly raised image thereon. The inked plates are rotated on a cylinder which transfers the image to the substrate. Flexography may be a relatively high-speed print process that uses fast-drying inks. In addition, flexography can be used to print continuous patterns on many types of absorbent and non-absorbent materials. Other embodiments may utilize gravure printing. More particularly, gravure printing utilizes an image etched on the surface of a metal plate. The etched area is filled with ink and the plate is rotated on a cylinder that transfers the image to the substrate. Still other embodiments may utilize ink jetprinting. Ink jet is a non-impact dot-matrix printing technology in which droplets of ink are jetted from a small aperture directly to a specified position on a media to create an image. Two examples of inkjet technologies include thermal bubble or bubble jet and piezoelectric. Thermal bubble uses heat to apply to the ink, while piezoelectric uses a crystal and an electric charge to apply the ink.

In addition to the aforementioned various types of printing processes, it is to be appreciated that various types of inks or ink systems may be applied to various types of substrates to create the disclosed patterns, such as solvent-based, water-based, and UV-cured inks. The primary difference among the ink systems is the method used for drying or curing the ink. For example, solvent-based and water-based inks are dried by evaporation, while UV-cured inks are cured by chemical reactions. Inks may also include components, such as solvents, colorants, resins, additives, and (for ultraviolet inks only) UV-curing compounds, that are responsible for various functions.

As shown in FIG. 1A, a method of printing graphics on absorbent articles 10 is provided. According to method 10, which comprises one or more of the following steps, a graphic is selected, the graphic's color(s) are determined, the substrate on which to print the graphic is selected, the size and layout of the graphic are manipulated to make it fit the area of the absorbent article it is to be printed on, and the graphic is printed on a substrate. These steps and additional optional steps are discussed in more detail herein. It is to be noted that, it will be appreciated by the skilled person that in alternate embodiments, some steps may be performed in a different order or they may be performed concurrently.

Figure 1B:
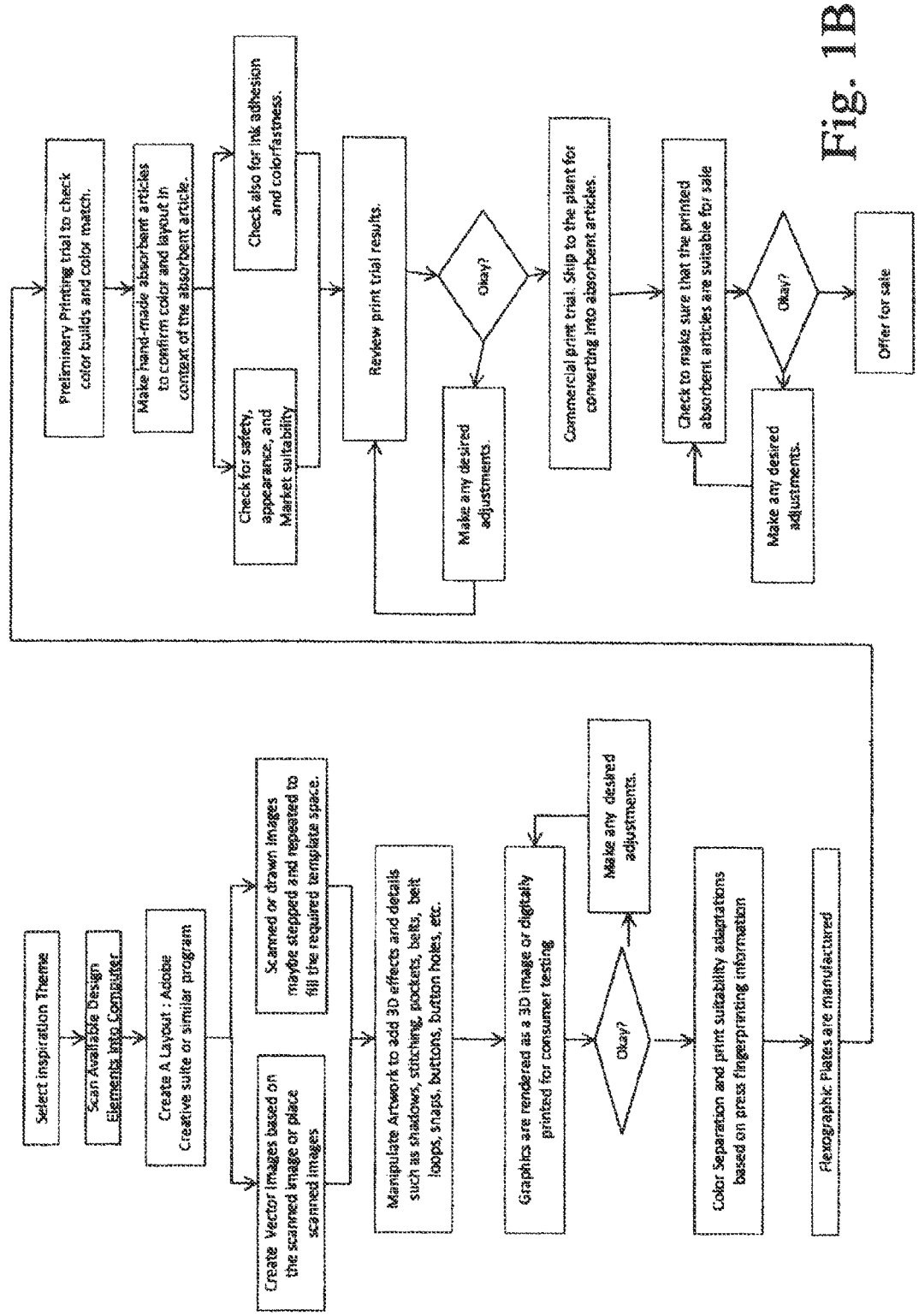
FIG. 1B is a flowchart of a method of printing graphics on absorbent articles suitable for use with the present invention.

As shown in FIG. 1B, a method of printing graphics on absorbent articles is provided. According to the method, which comprises one or more of the following steps, an inspirational theme is selected, available design elements are scanned into a computer file, a layout is created (using Adobe Creative Suite® or similar software), vector images are created based on the scanned image or scanned images are placed on a template of the absorbent article to be printed on, scanned or drawn images may be stepped and repeated to fill the space on a template of the absorbent article to be printed on, artwork is manipulated to add 3-dimensional effects and details, e.g. shadows, stitching, pockets, belts, belt loops, snaps, button, button holes, and the like, graphics are rendered as a 3-dimensional image or digitally printed for consumer testing, a determination is made of consumers' acceptance of the graphics, an editing loop is provided whereby any desired changes to improve consumer acceptance are made, color separation and print suitability adaptations are determined and made based on press fingerprinting information, flexographic plates are manufactured, a preliminary printing trial is conducted to check color builds and color match, hand-made absorbent articles are made to confirm color and layout in the context of the absorbent article, a check is conducted to check the safety, appearance, and market suitability of the absorbent articles, a check is conducted to check ink adhesion and colorfastness, print trial results are reviewed, a determination is made of whether the print trials were successful for the attributes measured, an editing loop is provided whereby any desired changes to improve success for the attributes measured are made, a commercial print trial is conducted wherein absorbent articles are shipped to a manufacturing plant for being converted into saleable absorbent articles, a check is conducted to check whether the printed absorbent articles are suitable for sale, a determination is made of whether the printed absorbent articles are suitable for sale based on the attributes measured, an editing loop is provided whereby any desired changes to improve success for the attributes measured are made, the printed absorbent articles suitable for sale are offered for sale. These steps and additional optional steps are discussed in more detail herein. It is to be noted that, it will be appreciated by the skilled person that in alternate embodiments, some steps may be performed in a different order or they may be performed concurrently.

Figure 3:
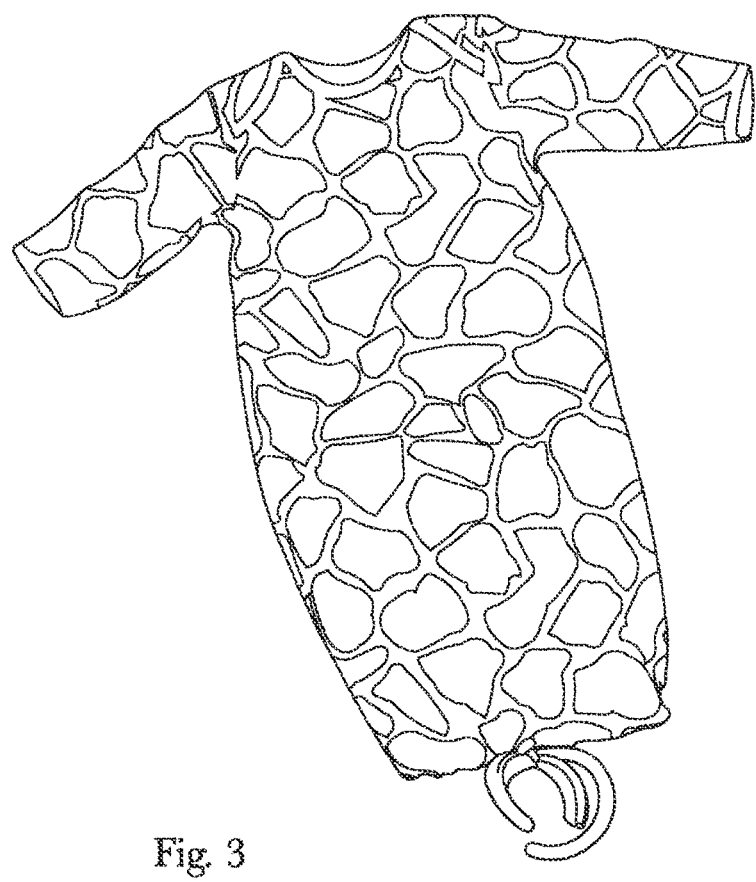
FIG. 3 is a perspective view of a design embodied in an article of clothing.
Figure 4:
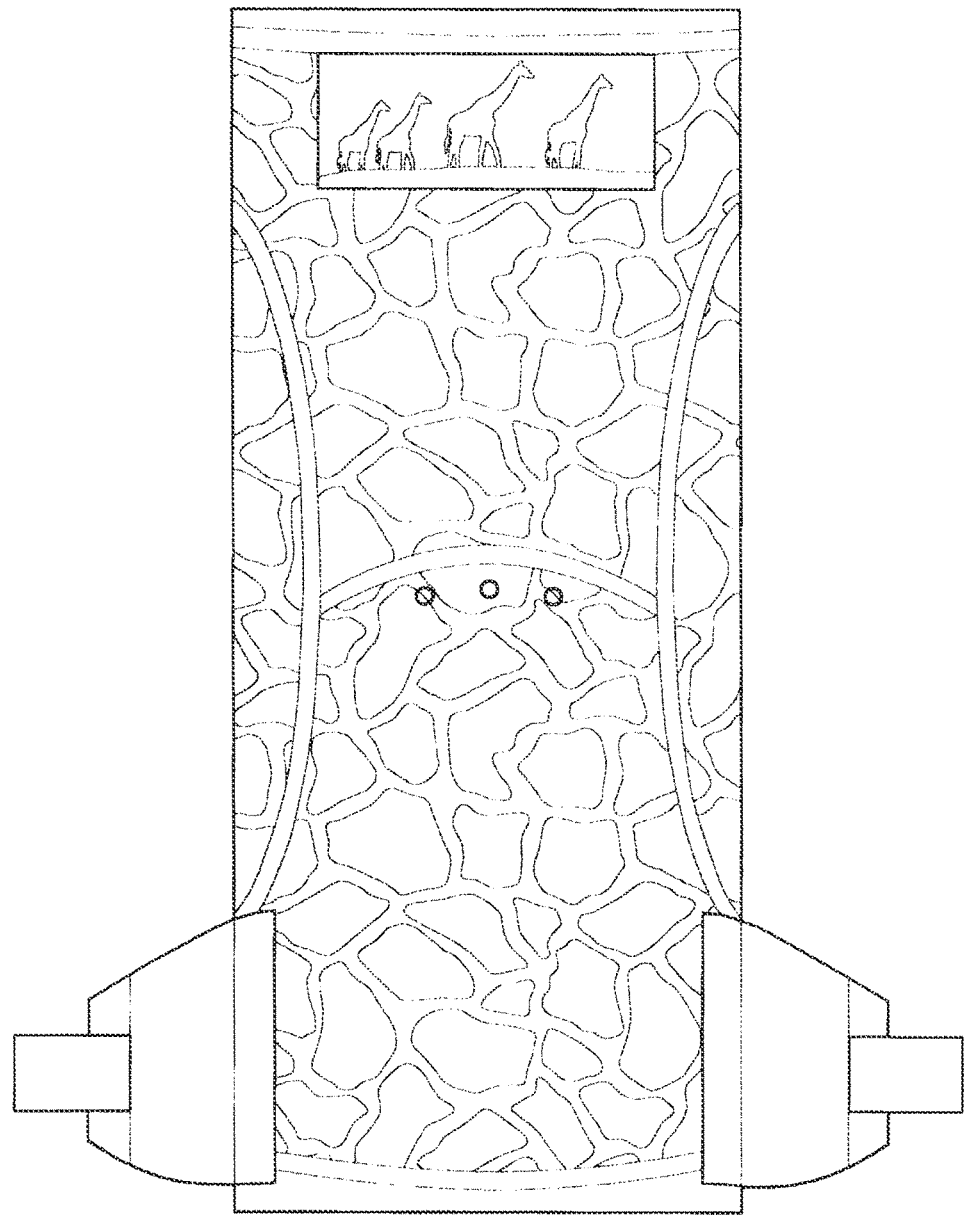
FIG. 4 is a perspective view of a design created using design software, inspired by a creator who views the graphics embodied in an article of clothing.
Figure 6:
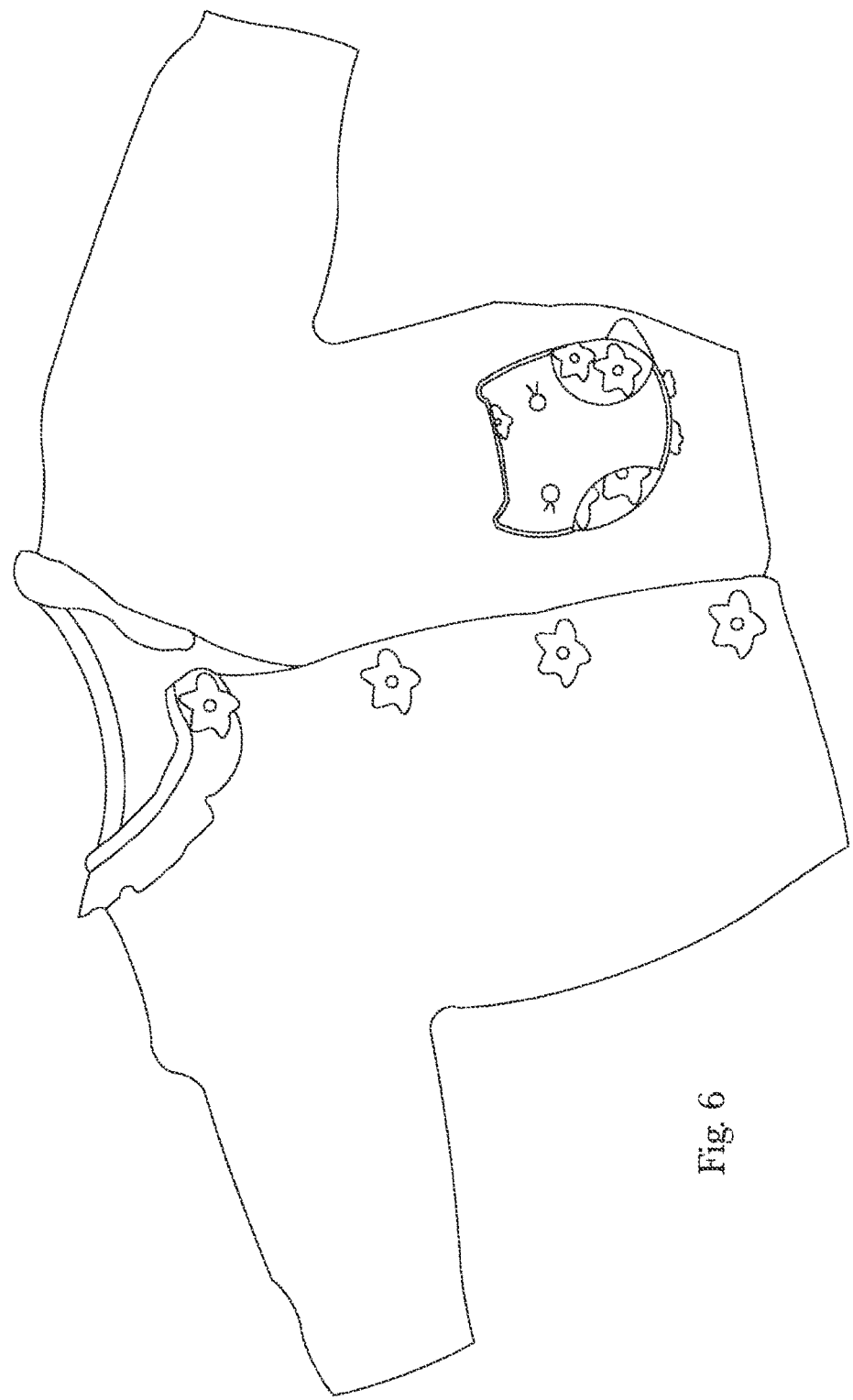
FIG. 6 is a perspective view of a design embodied in an article of clothing.
Figure 8:
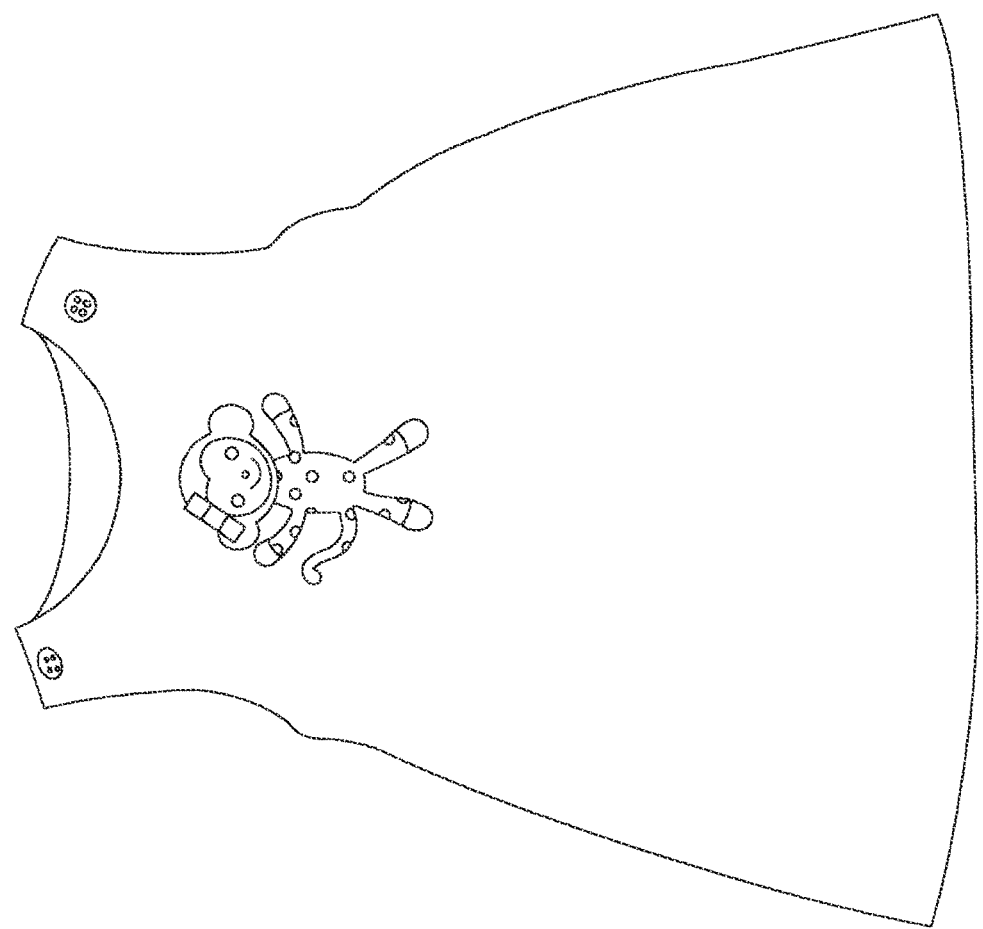
FIG. 8 is a perspective view of a design embodied in an article of clothing.

In selecting a graphic, the graphic may comprise one or more designs inspired by designs suitable for or actually embodied in fabric. The graphic may be embodied in an electronic file. Suitable file formats are JPG, JPEG, PNG, GIF, TIF (e.g. 8-bit, uncompressed). Preferably, the file will be less than 30 megabytes in size. The source of the graphic may vary. In certain embodiments of the invention, the design may be embodied in a fabric, an article of clothing, a clothing line, artwork, a painting, or the like. In any of the aforementioned embodiments, the graphic may be reduced in the form of a digital photograph, or in the form of an electronic scan. Examples of the design being embodied in an article of clothing are shown in FIGS. 3, 6, and 8. In yet another embodiment, the graphic is created using design software, e.g. Adobe Photoshop® or Adobe Illustrator®. In such an embodiment, the design may be created from scratch, or it may be inspired by a creator who has viewed the graphics embodied in a fabric, an article of clothing, a clothing line, artwork, a painting, or the like. An example of the design being created using design software, inspired by a creator who has viewed the graphics embodied in an article of clothing, is shown in FIG. 4.

The use of a higher quality file at this point in the process will typically result in a higher quality print ultimately being printed. In one embodiment, resolution of the image of the graphic embodied in the file will be at least 150 dpi (dots per inch). When flexographic printing is used, preferably the print size of an image to be printed, in pixel dimensions, will be 150 times the number of inches. Thus, for example, to ultimately print on an 8"×8" swatch, the image embodying the graphic will have a resolution of 1200 pixels×1200 pixels.

In an embodiment where the graphic is a scan of a design, suitable scanners will typically scan at 2400 dpi resolution or higher. Suitable scanners include the Epson® Expression® 10000XL, which is particularly useful when the graphic is embodied in a fabric.

Two colors are considered coordinated if they have first and second hues that are the same. Colors of different hues are also considered coordinated if they have a value (luminosity) difference of less than 5% of maximum, alternatively less than 3% of maximum or alternatively less than 1% of maximum. Colors of different hues are also considered coordinated if they have a saturation difference of less than 5% of maximum, alternatively less than 3% of maximum or alternatively less than 2.5% of maximum.

In an embodiment, color matching of visible surfaces is determined by the color of an absorbent article and the corresponding color of the clothing and/or line of clothing having a specified CIELab color space hue difference (ΔH). Characterizing color matching by the hue difference is desirable in that hue difference accounts for and considers all three dimensions within CIELab. While not being limited to this theory, such a three-dimensional measurement is believed to more fully characterize the difference in two colors.

Figure 2:
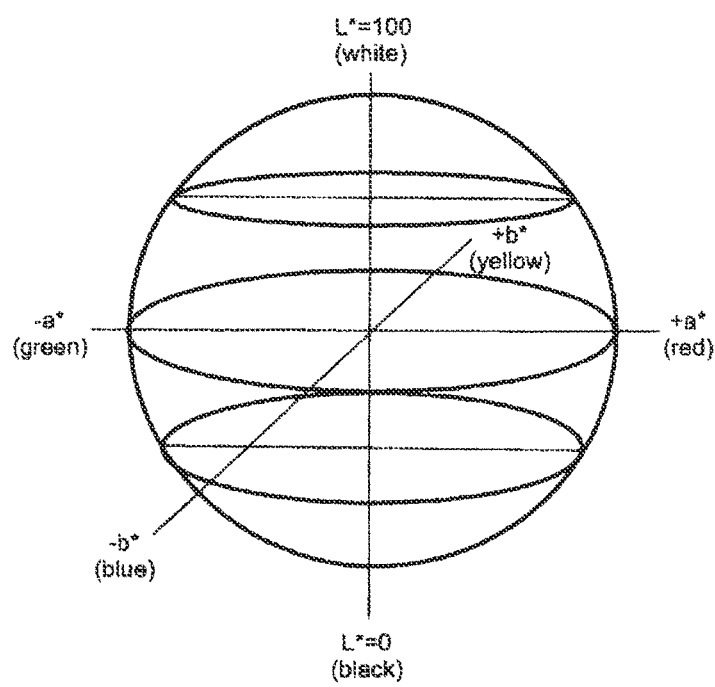
FIG. 2 is an illustration of three axes (respectively for the L*, a*, and b* value of a given color) used with the CIELAB color scale.

CIELAB is a conventional color model used to describe colors visible to the human eye. FIG. 2 is an illustration of three axes (respectively for the L*, a*, and b* value of a given color) used with the CIELAB color scale. When a color is defined according to the CIELAB color scale, L* represents lightness (0=black, 100=white), a* and b* independently each represent a two color axis, a* representing a red/green axis (+a=red, −a=green), while b* represents a yellow/blue axis (+b=yellow, −b=blue). The maximum for L* is 100, which represents a perfect reflecting diffuser, and the minimum for L* is zero, which represents black. The a* and b* axes have no specific numerical limits. The CIELAB color scale is an approximate uniform color scale, wherein the differences between points plotted in the color space correspond to visual differences between the colors plotted. Based on the L*, a*, and b* values for a first color (i.e. $L_1, a_1, b_1$) and a second color (i.e. $L_2, a_2, b_2$), the difference between the colors (i.e. ΔE) can be calculated using the following formula:

$$\Delta E = \sqrt{(\Delta L^{*2} + \Delta a^{*2} + \Delta b^{*2})}$$

wherein,
$\Delta L^* = L_1 - L_2$;
$\Delta a^* = a_1 - a_2$; and
$\Delta b^* = b_1 - b_2$.

The L*a*b* values for each zone of color in the graphic may be determined in various ways. For example, the L*a*b* values of the color zones may be determined by using ink with relatively known L*a*b* values. Alternatively, the L*a*b* values in a zone can be determined from the electronic file that is generated when a pattern is created. In such a case, the L*a*b* values may be obtained with a computer equipped with a software that can provide the L*a*b* value of a selected area. A non-limiting example of such software may be Adobe Photoshop®. In another embodiment, the L*a*b* values of various color zones on a graphic can be measured directly from the printed substrate that bears the design inspiring the graphic. A suitable procedure for measuring the L*a*b* values of a color zone is provided below.

In an embodiment, color measurements are performed using a commercial flat bed scanner capable of 4800 dpi, at 16 bit color depth, such as an Epson Perfection V500 Photo scanner (Epson America, Long Beach, Calif.). Each scan is calibrated against Pantone standards, and measurements made using Adobe Photoshop CS3 Extended Edition (Adobe Systems, Inc, San Jose, Calif.). The sample is measured on the printed side of the substrate. For example, if a laminate consist of a nonwoven and a film where the printing is on the film and sandwiched between the film and nonwoven, the nonwoven is removed before the printing on the film is measured.

Scans are calibrated using the Pantone Process Colors standard from the Pantone Formula Guide—Uncoated Papers (Pantone, Carlstadt, N.J.). CIE L*a*b* values are measured for the Pantone standard for each color, i.e., Process Yellow U, Process Magenta U, Process Cyan U, Process Black U, and the White uncoated paper. Tristimulus colors are measured according to ASTM Method E1164-07 (Standard Practice for Obtaining Spectrophotometric Data for Object-Color Evaluation) using a Hunter Labscan XE (HunterLab, Reston, Va.) with HunterLab Universal Software vs. 4.10 with the following settings: Scale CIELAB, 0/45 StdMode, Area View 0.50 in., Port Size 0.70 in., UV filter Nominal During measurement the standard is backed using the white calibration plate provided by HunterLab. To increase the reliability of the measurement, each color should be measured at least in triplicate and averaged. The sample is placed on the scanner with the printed-side toward the sensor. The Pantone standard is also placed on the scanner such that the sample and standard are both captured in the same image.

The scan is collected at 1200 dpi at 8 bit color depth into Photoshop for objects with a primary dimension of greater than 3 mm, and at 2400 dpi, 8 bit color depth for objects with a primary dimension of less than 3 mm. Within Photoshop, the image is transformed into a Lab, 8 bit image (note in this version of Photoshop, L*a*b* is imprecisely denoted as Lab). Using the "Levels" command, the L channel of the image is adjusted to read within 2 units for each of the yellow, magenta, cyan, black and white colors on the Pantone standard. L*a*b* values are measured using the Color Sampler Tool using an 11 by 11 average sample size.

The graphic may be selected to be printed on a suitable area for printing on any surface suitable for printing on the absorbent article. In an embodiment, the graphic is to be printed on the backsheet of an absorbent article. In another embodiment, it is to be printed on the ear of a diaper. In an embodiment, the substrate has a basis weight of less than or equal to 20 gsm.

In an embodiment, the substrate has a low modulus, i.e. ≤20 Newtons/cm. In another embodiment, the modulus of the substrate is from 16 to 20 N/cm. In another embodiment, the modulus is ≤16 N/cm. Applicants have learned that high winding speeds of 1000 feet per minute or more, along with various film properties, can impart defects into the wound layers of film during winding. For example, non-uniform tensions and/or pressures are oftentimes imparted to the film during winding (e.g., at the outermost wound layers and near the core of the roll) due to various factors such as tension variations in the winding device (e.g., tolerance run-outs in the winding cylinder), film stability at the winding device, caliper control of the film, etc. The resulting unevenness between the two wound layers (e.g., the outermost wound layer and an immediately underlying wound layer) can produce a wound-in defect(s) that later "grows" as multiple successive windings layers of the film are wound on top of the defect(s). These winding-induced defects can include: variations in print repeat length, tin can-type defects (e.g., the film roll exhibits a series of raised annular bands so as to resemble the side of a tin can), and gauge band types of defects. In this regard, while efforts are made to precisely design and build the mechanical components of the winding device, for large film width winding applications (e.g., on the order of 1 meter, 1.5 meters or even 2 meters or greater), unavoidable precision runouts tend to produce non-uniform tension during winding; in instances where the affected film layer is unable to readily move (or relax) relative to the immediately underlying layer (e.g., due to friction), one or more of the winding-induced defects mentioned above can occur. Winding defects are typically more frequently observed when the film is thin, has a low basis weight, and/or has a low modulus. In an embodiment, the film is has a thickness of ≤1 mm; preferably it is ≤0.75 mm. In an embodiment, the film has a basis weight of ≤20 gsm; preferably ≤16 gsm. In an embodiment, the film has a modulus of ≤20 N/cm; preferably about 16 N/cm. In an embodiment, the film is has a thickness of ≤1 mm, a basis weight of ≤20 gsm, and a modulus of ≤20 N/cm. In yet another embodiment, the film is has a thickness of ≤0.75 mm, a basis weight of ≤16 gsm, and a modulus of 16 N/cm.

The size and layout of the graphic are manipulated to make it fit the area of the absorbent article it is to be printed on. The graphic can be centered on a template of the area to be printed, e.g. the diaper backsheet, by any suitable process that obtains the desired color and shape of the graphic for the given print area. In an embodiment, a designer alters the size or dimensions of the graphic to fit the area of the absorbent article substrate to be printed on. This typically involves cropping, enlarging/decreasing the overall dimensions of the graphic, and may involve modifying the graphic itself by introducing or removing design features of the graphic in order to make it fit the print area. Care should be taken not to modify the graphic in a way that causes too much detail to be lost.

The difference between the colors (i.e. ΔE) can be used to compare the colors graphic being printed versus target, e.g. when conducting test prints. In one embodiment, the ΔE between the graphic being printed and the original design is less than 16. In another embodiment, the ΔE between the graphic being printed and the original design is less than 12. In yet another embodiment, the ΔE between the graphic being printed and the original design is less than 9.

Figure 5:
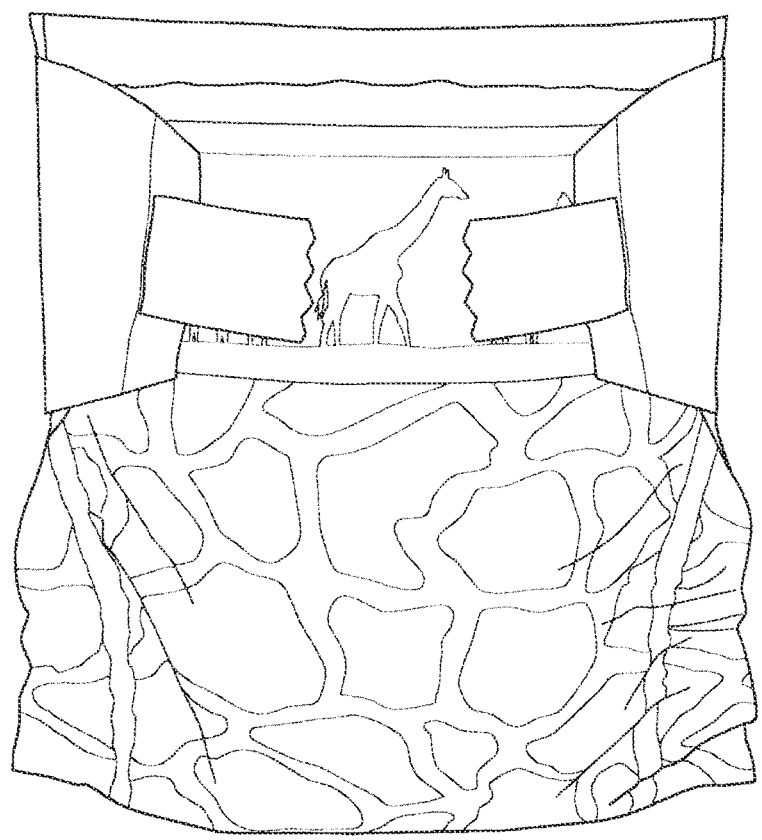
FIG. 5 is a perspective view of a graphic printed on a diaper that is inspired by the design shown in either of FIG. 3 or 4.
Figure 7A:
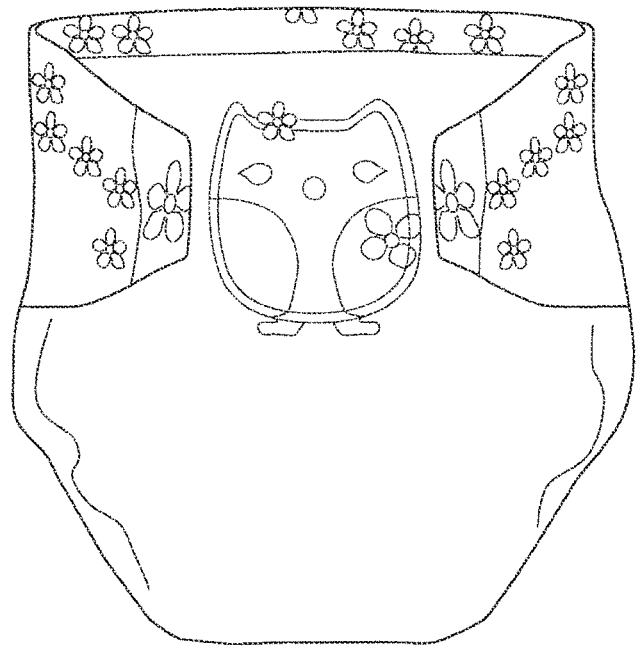
FIGS. 7A and 7B are perspective views of graphics printed on diapers that are inspired by the design shown in FIG. 6.
Figure 7B:
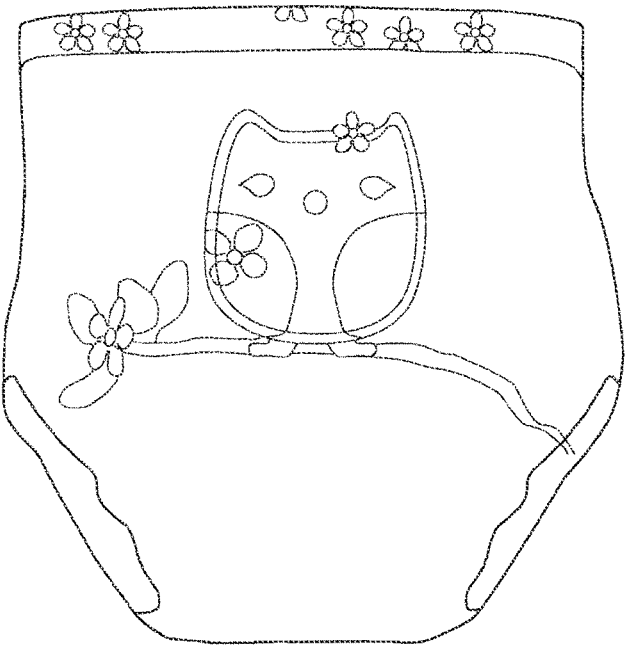
Figure 9B:
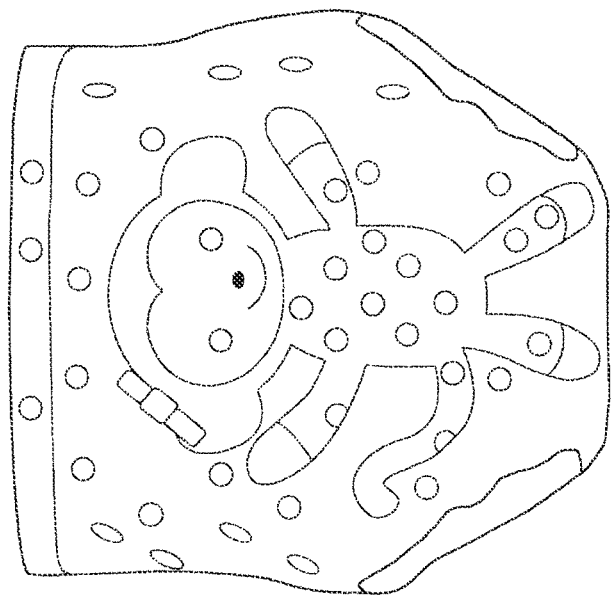
FIGS. 9A and 9B are perspective views of graphics printed on diapers that are inspired by the design shown in FIG. 8.
Figure 9A:
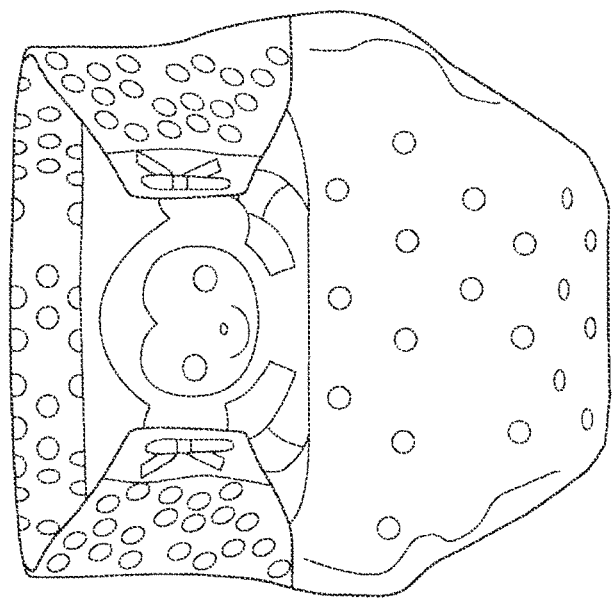

The graphic is printed on a substrate. FIG. 5 shows a graphic printed on a diaper that was inspired by the design shown in either of FIG. 3 or 4. FIGS. 7A and 7B show a graphics printed on diapers that were inspired by the design shown in FIG. 6. FIGS. 9A and 9B show graphics printed on diapers that were inspired by the design shown in FIG. 8.

Optionally, one or more test prints are done. Settings may be adjusted, e.g. color, size, and/or shape, after each successive test print until the desired color and appearance of the graphic are obtained. One factor to consider in adjusting settings is to compare the colors and density of the graphic being printed versus target. Colors may be printed by using a variety of methods. Some suitable methods are single spot color; 4-color process printing (using cyan, magenta, yellow, and black; also known as "CMYK"); expanded color gamut 6-color or 7-color (CMYK+orange, green, and violet; also known as "OGV"); or a combination of 4-color, 6 color, or 7 color process printing with spot color printing. In an embodiment, 7 color process printing is combined with spot color printing. Additional factors to consider in adjusting settings are the shape and layout of the graphic. This may also include color-to-color alignment. Yet another factor to consider in adjusting settings is ink adhesion, e.g. how well it resists rub-off and/or leaching.

In an embodiment, the graphic is printed using a flexographic press. The flexographic generally operates by transferring ink from a soft rubber transfer roller to an anilox roll; this roll is filled with billions of tiny cells. Once they are filled, a doctor blade is used to scrape away any excess ink from the surface of the roller; this meters the quantity of ink to reach the printing plate. Ink is spread evenly on the anilox rollers to transfer ink to the raised parts of the flexible printing plate. The printing plate is wrapped around a plate cylinder. The raised sections of a flexographic printing plate are coated with ink ready to be pressed on the material to be printed. An impression cylinder presses the substrate (film) to be printed against the printing plate. The raised sections of the printing plate transfer their ink coating to the material being printed. The ink is dried. Each ink color requires its own anilox inking rollers, plate and cylinder, and colors are printed one after the other on to the material as it passes through the press.

In an embodiment, the flexographic press has a color-to-color registration accuracy of ±0.04 mm. Such a press is the ASTRAFLEX®, available from Windmoeller & Hoelscher Corp. Accordingly, by using a flexographic press with such accuracy in color-to-color registration, graphics may be printed having very narrow lines as fine as ≤0.032 inch in width, preferably 0.020 inch. Also suitable are flexographic presses known as the NOVOFLEX® and VISTAFLEX® (both available from W&H).

Suitable printing plates are typically made from one or more photopolymers and are typically supplied in flat sheets of un-reacted polymer. They are then processed by specialist pre-press houses. The use of a higher quality plate at this point in the process will typically result in a higher quality print ultimately being printed. Raised areas of the plate transfer the ink. In an embodiment, the relief is up to and including 0.8 mm in height. In an embodiment, the total thickness of the plate is from 1.3 to 1.7 mm, preferably 1.5 mm. In various embodiments, the thickness of the plate is selected from 1.14 mm (0.045"), 1.70 mm (0.067"), 2.28 mm (0.090"), 2.54 mm (0.100"), 2.72 mm (0.107"), and 2.84 mm (0.112"). In an embodiment, the thickness of the plate is 1.70 mm (0.067") with a relief of 0.020 inch. In another embodiment, the thickness of the plate is 1.70 mm (0.067") with a relief of 0.025 inch.

The anilox and doctor blade meter an even amount of ink to the printing plate. The ink is held in the billions of anilox cells while the doctor blade runs over the surface of the anilox removing any excess ink. The anilox is typically manufactured from a ceramic compound whose hardness provides long life and is resistant to abrasion from the doctor blade. The anilox roll is manufactured to release a certain ink weight from the laser engraved cells, so the size of the cells and resolution are important to the color on the final printed image.

There are two main types of ink supply and doctoring system used in flexography. In open systems the anilox rotates in an open bath of ink and the doctor blade meters the ink just prior to the ink being transferred to the plate cylinder.

The Chamber system encloses the ink using two blades within a chamber. The retaining blade at the bottom acts as a seal while the doctor blade at the top performs the ink metering. The ink is pumped through the system to maintaining a constant supply of ink to the anilox surface. Advantageously, the closed doctoring system requires less ink to "charge" the system and there is no release of VOC's, as the system is contained.

In an embodiment, the flexographic printing press comprises from 2 to 10 stations. These include but are not limited to three main configurations, the central impression press, the in-line press, and the stack press.

A web passes around the central impression (CI) cylinder with each color being printed in turn. Inter-station driers are used to cure the inks between print stations to ensure wet on dry printing. An advantage of this type of press is that registration is excellent, as the web is held over the CI drum between print stations. There is less chance of the substrate being extended between the print stations. The press speed of central impression presses can generally be increased beyond that of the other press types.

The in line press is a combination of individual units with a small distance between the print heads. Each color is printed on the web fed substrate. Each color has an individual impression cylinder against which the plate is pressed. An advantage of the in line press is that other printing technologies (such as rotary screen or gravure) and additional colors/processes can be incorporated by simply adding another station. These machines often use UV inks which are dried between each print station.

When using flexographic printing, certain management of the surface energy of print tools and substrates and the surface tension of the inks can lead to unexpected results. The surface tension/energy of the components of the printing process are advantageously arranged such that it increases from the inks, to anilox, to plates, to substrates. In one embodiment, the difference in surface tension/energy between the inks and the substrates is from 10 to 14 dynes, preferably 12 dynes/cm.

A design will typically comprise various design elements of the absorbent article. Design elements may be physical features of the absorbent article, such as the overall outline, location of tabs, fasteners, borders, junctions of materials, stitching, and like elements. Design elements may also be either actual physical features of the absorbent article or elements that are not actual physical features but are to be printed on the absorbent article to make it appear that they are actual elements of the absorbent article, non-limiting examples of features that may fall within either or both of these groups include: printing borders, seams, pockets, zippers, zipper flaps, topstitching, embossment, quilting, buttons, bows, ribbons, straps, snaps, belt loops, suspenders, sales tags, etc.

A design may also be themed or exhibit an otherwise like group of colors and patterns and/or solid prints. In an embodiment, they may be selected from groups being categorized as being gender neutral, boy appropriate, or girl appropriate. In another embodiment, they may be selected from groups categorized as being sporty, outdoors, sophisticated, professional, casual, cute, sassy, feminine (e.g. quilted, paisley, curly cues, polka dots), fresh, seasonal (e.g. spring, summer, fall, winter), patriotic, weather/climatic (e.g. sunny, rainy, snowy), ethnic, soft tones, earth tones, pastels, rock 'n roll, western (e.g. cowboy/cowgirl), animal, plant, food, or industrial.

The hue difference represents the distance between two points within CIELab color space. The CIELab color space hue difference ($\Delta H$) for a first color ($L^*_1$, $a^*_1$, $b^*_1$) and a second color ($L^*_2$, $a^*_2$, $b^*_2$), is calculated according to the following formula: $\Delta H = \sqrt{(\Delta E)^2 - (\Delta C)^2 - (\Delta L^*)^2}$. Within said formula, $\Delta E$ is the CIELab color space total color difference between the two colors and is calculated as presented above. The $\Delta C$ is the CIELab color space chroma difference between the two colors and is calculated by:

$$\Delta C = \sqrt{a_2^{*2} + b_2^{*2}} - \sqrt{a_1^{*2} + b_1^{*2}}.$$

The $\Delta L^*$ is the difference in $L^*$ values between the two colors and is calculated by: $\Delta L^* = L^*_2 - L^*_1$.

In an embodiment, at least two visible surfaces each comprising an imparted color will have a CIELab color space hue difference of ≤4 in order to be considered matching. In another embodiment, the difference will be ≤3. In yet another embodiment, the difference will be ≤2. The visible surfaces are analyzed according to the Test Method described below. Upon analysis, the inherent color of an element comprising a visible surface will yield $L^*$, $a^*$, and $b^*$ coordinates. Two elements are selected and the L*, a*, and b* values of the elements are inserted into the formula presented above to result in a hue difference.

Visible surfaces are tested in a dry state and at an ambient humidity of approximately 50%±2%. Reflectance color is measured using the Hunter Lab LabScan XE reflectance spectrophotometer obtained from Hunter Associates Laboratory of Reston, Va. The spectrophotometer is set to the CIELab color scale and with a D50 illumination. The Observer is set at 10° and the Mode is set at 45/0°. Area View is set to 0.125" and Port Size is set to 0.20" for films; Area View is set to 1.00" and Port Size is set to 1.20" for nonwovens and other materials. The spectrophotometer is calibrated prior to sample analysis utilizing the black and white reference tiles supplied from the vendor with the instrument. Calibration is done according to the manufacturer's instructions as set forth in LabScan XE User's Manual, Manual Version 1.1, August 2001, A60-1010-862. If cleaning is required of the reference tiles or samples, only tissues that do not contain embossing, lotion, or brighteners should be used (e.g., Puffs® tissue). Any sample point on the visible surface of the element containing the imparted color to be analyzed should be selected. Typically, sample points are selected so as to be close in perceived color. A single ply of the element is placed over the spectrophotometer's sample port. A single ply, as used within the test method, means that the visible surface of the element is not folded. Thus, a single ply of a visible surface may include the sampling of a laminate, which itself is comprised of more than one lamina. The sample point comprising the color to be analyzed must be larger than the sample port to ensure accurate measurements. A white tile, as supplied by the manufacturer, is placed behind the visible surface. The L*, a*, and b* values are read and recorded. The visible surface is removed and repositioned so that a minimum of six readings are obtained for the visible surface. If possible (e.g., the size of the imparted color on the element in question does not limit the ability to have six discretely different, non-overlapping sample points), each of the readings is to be performed at a substantially different region on the visible surface so that no two sample points overlap. If the size of the imparted color region requires overlapping of sample points, only six samples should be taken with the sample points selected to minimize overlap between any two sample points. The readings are averaged to yield the reported L*, a*, and b* values for a specified color on a visible surface of an element.

Coordination in the present invention may also contain commonly used color schemes which tend to harmonize or coordinate. That is, the first and second visual color characteristics may be selected to enhance the visual coordination in addition to having at least a first and second color as the first and second visual characteristics. Examples of these color schemes include, for example, monochromatic color, complementary colors, analogous colors, warm and cool colors, neutral colors, color contrast, tetradic color scheme, triad color scheme or other chord color schemes. Monochromatic color scheme uses one base color but varies the color tint, shade and/or tone. Complementary colors are colors which are opposite each other on a color wheel. Analogous colors are colors which are adjacent each other on the color wheel. Warm and cool color schemes use three colors, two of which are warm colors and one is cool color or two cool colors and one warm color. Warm colors are generally associated with fire and the sun, for example, red, yellow and orange and cool colors are generally associated with water the sky and foliage, for example green, blue and violet. Neutral color coordination includes using shades of black, white, gray and beige together. Color contrast scheme include using dark and light colors together. Tetradic is a four color scheme and a triad color scheme is a three color scheme, both of which are known to those skilled in the art. Any of these color schemes may be used in the present invention to help coordinate and harmonize two or more colors as the visual characteristics in the present invention.

Coordination may be created by providing a theme on the absorbent article that matches the theme embodied in an article of clothing and/or line of clothing. Non-limiting examples of themes include: sporty, outdoors, sophisticated, professional, casual, cute, sassy, feminine (e.g. quilted, paisley, curly cues, polka dots), fresh, seasonal (e.g. spring, summer, fall, winter), patriotic, weather/climatic (e.g. sunny, rainy, snowy), ethnic, soft tones, earth tones, pastels, rock 'n roll, western (e.g. cowboy/cowgirl), animal, plant, food, or industrial.

Two patterns are considered coordinated when they have substantially the same pattern elements, regardless of other factors such as orientation. To gain a better understanding of how patterns are considered to be coordinated within the scope of the present invention, reference is made to FIGS. 3 to 5. In FIG. 3, an article of clothing, a child's sleeper, is shown. Certain visual characteristics exhibited on the sleeper include the giraffe spots, the pattern of giraffe spots, and the color (depicted by gray shading). In FIG. 4, a print out of a graphic design file showing the graphic being developed for printing on an absorbent article, is shown. The graphic design file shows giraffe spots as the sleeper, the same pattern of giraffe spots as the sleeper, and the same color (depicted by gray shading) as the sleeper, with the addition of a visual characteristic of four giraffes that appear to be standing or walking. FIG. 5, an absorbent article, a diaper with a graphic printed on it, is shown. The diaper shows giraffe spots as does the sleeper, a portion of the same pattern of giraffe spots as the sleeper, and the same color (depicted by gray shading) as the sleeper, and the additional visual characteristic of giraffes that appear to be standing or walking as does the graphic design file. These several visual characteristics are coordinated, e.g., substantially the same shape, even though they are of different sizes, and the graphic design file and printed diaper share a common visual characteristic that is not shared by the original sleeper. Summarily, referring to FIGS. 3 to 5, elements of the clothing article, a sleeper is configured with a shape, the giraffe spots, a pattern, the particular arrangement of giraffe spots, and a certain color of spots, while the absorbent article, a printed diaper, is configured with a coordinated shape of giraffe spots, coordinated pattern of arranged giraffe spots, coordinated color, and a further visual characteristic that is similar to the previous elements, depictions of giraffes. The clothing and the absorbent article are coordinated, even though they are of different sizes and notwithstanding that an additional elements, the giraffes, are also present on the printed diaper. Stated another way, in the present invention, clothing and an absorbent article are considered coordinated if they have the same or similar visual characteristics, whether the visual characteristics are matched identically or similarly matched. It is further noted that patterns are considered coordinated if there are pattern elements which are the same or similar, even if additional pattern elements are present.

In one embodiment, there are at least two different types of visual characteristics. One particular combination is the use of color and pattern. As set forth above, the more shared visual characteristics there are, the more coordinated the absorbent article and article of clothing and/or line of clothing will appear.

In order to obtain a better understanding of the present invention, attention is directed to FIGS. 6, 7A, and 7B. In FIG.

6, an article of clothing, a child's sweater, is shown. Certain visual characteristics exhibited on the sweater include an owl, white as a coordinating color, a flower pattern on the owl's wings, the color of the owl's body (depicted by gray shading), and the owl being embroidered. In FIGS. 7A and 7B, diapers with graphics printed on them, are shown. The diapers shows an owl as does the sweater, white as a coordinating color, a substantially similar flower pattern on the owl's wings as the sweater, the same color of the owl's body (depicted by gray shading) as the sweater, the owl having an embroidered appearance, and the additional visual characteristics of a substantially similar flower pattern being printed on the fasteners of the diaper (in FIG. 7A) or of a branch upon which the owl appears to be sitting (in FIG. 7B). These several visual characteristics are coordinated, e.g., substantially the same shape, even though they are of different sizes, and printed diapers have a visual characteristic that is not shared with the original sweater. Summarily, referring to FIGS. 6, 7A, and 7B, elements of the clothing article, a sweater, is configured with a animal character (an owl), a coordinating color (white), a pattern (the flower pattern on the owl's wings), the color of the owl's body (depicted by gray shading), and a texture (the owl being embroidered), while the absorbent article (a printed diaper) is configured with a coordinated animal character (an owl), a coordinated coordinating color (white), a coordinated pattern (the flower pattern on the owl's wings), a coordinated color of the owl's body (depicted by gray shading), and a coordinated texture (the owl being embroidered), and further visual characteristic that are similar to the previous elements, substantially similar flower pattern being printed on the fasteners of the diaper (in FIG. 7A) or of a branch upon which the owl appears to be sitting. The clothing and the absorbent article are coordinated, even though they are of different sizes and notwithstanding that an additional elements, the flower pattern and the branch, are also present on the printed diaper.

In order to obtain a better understanding of the present invention, attention is directed to FIGS. 8, 9A, and 9B. In FIG. 8, an article of clothing, a child's dress, is shown. Certain visual characteristics exhibited on the dress include a monkey, a bow on the monkey's ear, the color of the monkey's body, having light colored paws (depicted by gray shading), the monkey being embroidered, and the torso, arms, and legs of the monkey being dotted. In FIGS. 9A and 9B, diapers with graphics printed on them, are shown. The diapers show a monkey as does the dress, a bow on the monkey's ear, the color of the monkey's body, having light colored paws (depicted by gray shading), the monkey being embroidered, and the torso, arms, and legs of the monkey being dotted, and the additional visual characteristics of the monkey appearing to be partially inserted into a pocket (in FIG. 9A). These several visual characteristics are coordinated, e.g., substantially the same shape, even though they are of different sizes, and one of the printed diapers has a visual characteristic that is not shared with the original dress, and in fact, both of the printed diapers have a different background color than the original dress. Summarily, referring to FIGS. 8, 9A, and 9B, a clothing article, a dress, is configured with an animal character (a monkey), a pattern (bow on the monkey's ear), color (the color of the monkey's body, having light colored paws (depicted by gray shading)), texture (the monkey being embroidered), and another pattern (the torso, arms, and legs of the monkey being dotted), while the absorbent article (a printed diaper) is configured with a coordinated animal character (a monkey), a coordinated pattern (bow on the monkey's ear), a coordinated color (the color of the monkey's body, having light colored paws (depicted by gray shading)), a coordinated texture (the monkey being embroidered), and another coordinated pattern (the torso, arms, and legs of the monkey being dotted)), and further visual characteristic that are similar to the previous elements, the monkey appearing to be partially inserted into a pocket (in FIG. 9A) and both of the printed diapers having a different background color than the original dress (FIGS. 9A and 9B). The clothing and the absorbent article are coordinated, even though they are of different sizes and notwithstanding that an additional elements, the pocket and the different background color, are present on the printed diaper.

In various embodiments, the first visual characteristic may be a color and the second visual characteristic may be different colors embodied in an article of clothing and/or a line of clothing, with both of the colors applied to the absorbent article. In another embodiment, the first visual characteristic may be a color, and the second visual characteristic may be an embossment, pattern, or shape (e.g., fastening element). In yet another embodiment, the first visual characteristic may be a first embossment, printing or dyeing pattern and the second visual characteristic may be a second embossment, printing or dyeing pattern.

Embossing is an effective way to impart texture and pattern visual characteristics to an absorbent article. The embossing pattern may be a high density embossing pattern, or a low density embossing pattern, both of which may be registered or non-registered.

Additional examples of visual characteristics include: the location and appearance of tabs, fasteners, borders, junctions of materials, stitching, printing borders, seams, pockets, zippers, zipper flaps, topstitching, embossment, quilting, buttons, bows, ribbons, straps, snaps, belt loops, suspenders, and the like.

In an embodiment, a method of selling absorbent articles bearing at least one graphic, wherein at least one visual characteristic of the at least one graphic is visually coordinated to at least one visual characteristic of an article of clothing and/or a line of clothing is provided. It should be understood that the method relates to the offer to sell such absorbents articles as well as actually selling them.

According to the method, absorbent articles visually coordinated to an article of clothing and/or a line of clothing are sold. Such articles are described above. In an embodiment, the article of clothing to which the absorbent article is being coordinated, is a stand-alone, or single item of clothing, e.g. being sold by one or more retailers. In another embodiment, the article of clothing is one article in a line of clothing being sold by one or more retailers. In yet another embodiment, the absorbent article is visually coordinated to a whole or portion of a whole clothing line. In such an embodiment, the visual characteristics being coordinated to will be embodied in several of articles of clothing in a line of clothing. Such visual characteristics will be common among at least a few of the articles of clothing in the line, and may be, in the fashion sense, consider the signature elements of the line. In an embodiment, such visual characteristics that are signature elements are not characters from story books, nursery rhymes, television shows, movies, comic books, cartoons, and the like. In another embodiment, such visual characteristics that are signature elements are designed by a fashion designer.

In an embodiment, a retailer sells absorbent articles that are visually coordinated to an article of clothing that the retailer sells. In another embodiment, a retailer exclusively sells absorbent articles that are visually coordinated to an article of clothing that the retailer exclusively sells. In an embodiment, a retailer sells absorbent articles that are visually coordinated to a line of clothing that the retailer sells. In an embodiment, a retailer exclusively sells absorbent articles that are visually coordinated to a line of clothing that the retailer exclusively sells. In various embodiments, any or all of the selling steps disclosed in this paragraph may be conducted in-store, on-line, or a combination of both. The term "on-line" is intended to include any e-commerce medium, e.g. internet, wireless internet, websites, mimics of any of the preceding that are embodied in personal digital devices including smart phones, and the like.

Collections of absorbent articles comprise a plurality of design graphics, preferably from 2 to 6, more preferably from 2 to 4, that are visually coordinated to an article of clothing, and/or a line of clothing. It is contemplated that an entire collection or fewer than an entire collection may be sold contemporaneously. In an embodiment, absorbent articles in a collection are co-packaged. Co-packaged means sold together at the same time. This may be accomplished, e.g. in store, by actually placing the similar and/or related graphic absorbent articles in the same primary package, e.g. a polybag made of, e.g. polyethylene, polypropylene, or mixtures or laminates thereof, by placing them in separate primary packages that are then placed together into a secondary package, e.g. a cardboard box containing both polybags, by securing separate primary packaging to each other, e.g. adhesive or physical binding means, e.g. string or tape, or other suitable means for ensuring that the absorbent articles are sold ultimately as a unit. Accordingly, in an embodiment, the method may provide for: (a) selecting a plurality of design graphics from a collection; (b) printing sets of absorbent articles, each bearing a different design graphic selected in the previous step; (c) co-packaging the sets of absorbent articles; and (d) offering the co-packaged sets for sale. The skilled person will appreciate that in the embodiment just described, any or all of the steps typically carried out by a manufacturer or a retailer of the absorbent articles, may be performed by an agent or designee thereof.

This may be accomplished, e.g. online, by making available any of the aforementioned co-packaged executions, by allowing a purchaser to "click on" combinations that will ultimately be co-packaged prior to shipping to the purchaser, or other suitable means for ensuring that the absorbent articles are sold ultimately as a unit. It is contemplated that by allowing a purchaser to "click on" combinations that will ultimately be co-packaged prior to shipping to the purchaser, a significant degree of customization of the order may take place. Accordingly, in an embodiment, the method may provide for: (a) a manufacturer or a retailer, allowing a purchaser to select a plurality of design graphics from a collection; (b) the manufacturer printing sets of absorbent articles, each bearing a different design graphic selected by the purchasers; (c) the manufacturer co-packaging the sets of absorbent articles; and (d) making the co-packaged sets available to the purchaser. The skilled person will appreciate that in the embodiment just described, any or all of the steps being carried out by a manufacturer or a retailer, or even a purchaser, may be performed by an agent or designee thereof. Furthermore, the step of making available to the purchaser may include sending the sets of absorbent articles to a benefactor of the purchaser, e.g. as a gift.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of printing a graphic on an absorbent article comprising the steps of:
   a. selecting a graphic wherein at least one visual characteristic of the graphic is visually coordinated to at least one visual characteristic of an article of clothing, the at least one visual characteristic being color, texture, pattern, or form, and the article of clothing being part of a series of related clothing items that constitute a line of clothing;
   b. embodying the selected graphic in an electronic file;
   c. selecting a substrate on which to print the graphic;
   d. manipulating the size and layout of the graphic to make it fit the area of the absorbent article it is to be printed on; and
   e. printing the graphic on the substrate;
   wherein the absorbent article comprises a topsheet having a bodyfacing surface and a garment facing surface, a backsheet having a bodyfacing surface and a garment facing surface, and an absorbent core disposed between the garment facing surface of the topsheet and the bodyfacing surface of the backsheet; and
   wherein the absorbent article is visually coordinated to a whole or a portion of the whole series of related clothing items that constitute the line of clothing.

2. The method of claim 1, wherein the graphic matches at least one visual characteristic of the article of clothing.

3. The method of claim 1, wherein the absorbent articles are selected from the group consisting of diapers, feminine pads, pantiliners, tampons, and incontinence pads.

4. The method of claim 3, wherein the absorbent articles are diapers.

5. The method of claim 3, wherein the absorbent articles are selected from the group consisting of feminine pads, pantiliners, and tampons.

6. The method of claim 3, wherein the absorbent articles are incontinence pads.

7. The method of claim 1, wherein the substrate is a nonwoven fabric or web.

8. The method of claim 1, wherein the substrate is a polyolefin film.

9. The method of claim 1, wherein the graphic is disposed on the bodyfacing surface of the topsheet.

10. The method of claim 1, wherein the graphic is disposed on the garment facing surface of the topsheet.

11. The method of claim 1, wherein the graphic is disposed on the bodyfacing surface of the backsheet.

12. The method of claim 1, wherein the graphic is disposed on the garment facing surface of the backsheet.

13. The method of claim 1, wherein the absorbent article comprises a compressed absorbent core disposed within an overwrap substantially covering the exterior surface of the compressed absorbent core, the overwrap having a core facing surface and a bodyfacing surface.

14. The method of claim 13, wherein the graphic is disposed on the core facing surface of the overwrap.

15. The method of claim 13, wherein the graphic is disposed on the bodyfacing surface of the overwrap.

16. The method of claim 13, wherein the graphic is disposed on both the core facing surface of the overwrap and the bodyfacing surface of the overwrap.

17. The method of claim 1, wherein step (b) is performed by a user creating an image of the graphic with design software, the resolution of the image of the graphic in the electronic file being about 150 dpi or greater.

18. The method of claim 1, wherein step (b) is performed by creating an image of the graphic with a scanner, the resolution of the image of the graphic in the electronic file being about 2400 dpi or greater.

19. The method of claim 1, wherein the at least one visual characteristic of the graphic is color, and the color of the selected graphic and the color of the printed graphic have a CIELab color space difference ($\Delta E$) of about 16 or less, wherein the color difference for a first color ($L_1, a_1, b_1$) and a second color ($L_2, a_2, b_2$), is calculated according to the following formula: $\Delta E = \sqrt{(\Delta L^2 + \Delta a^2 + \Delta b^2)}$ wherein: $\Delta L = L_1 - L_2$; $\Delta a = a_1 - a_2$; and $\Delta b = b_1 - b_2$.

20. The method of claim 1, wherein the substrate has a modulus of about 20 N/cm or less.

21. The method of claim 1, wherein the graphic is printed on the substrate using a flexographic press.

22. The method of claim 1, wherein the absorbent article comprises an ear, and the graphic is disposed on the ear.

* * * * *